United States Patent [19]

Gotthardt

[11] Patent Number: 4,942,876
[45] Date of Patent: Jul. 24, 1990

[54] PACEMAKER TERMINAL APPARATUS

[75] Inventor: Gerhard R. Gotthardt, Castle Hill, Australia

[73] Assignee: Telectronics, N.V., Curacao, Netherlands Antilles

[21] Appl. No.: 227,546

[22] Filed: Aug. 2, 1988

[51] Int. Cl.⁵ .............................................. A61N 1/00
[52] U.S. Cl. ................................ 128/419 P; 439/817
[58] Field of Search ................. 128/419 P, 784, 639, 128/641, 642; 439/817, 819

[56] References Cited

U.S. PATENT DOCUMENTS

| | | | |
|---|---|---|---|
| 2,424,444 | 7/1947 | Fox | 439/817 |
| 2,701,871 | 2/1955 | Rauch | 439/817 |
| 3,806,860 | 4/1974 | Flammini | 439/817 |
| 4,112,953 | 9/1978 | Shanker et al. | 128/419 P |
| 4,347,849 | 9/1982 | Congdon | 128/419 P |
| 4,445,511 | 5/1984 | Cowdery et al. | 128/419 P |
| 4,466,441 | 8/1984 | Skubitz et al. | 128/419 PS |
| 4,541,681 | 9/1985 | Dorman et al. | 439/429 |
| 4,619,058 | 10/1986 | Gumbert | 24/117 |
| 4,672,979 | 6/1987 | Pohndorf | 128/419 P |

Primary Examiner—Max Hindenburg
Assistant Examiner—Kennedy J. Schaetzle
Attorney, Agent, or Firm—Finnegan, Henderson, Farabow, Garrett & Dunner

[57] ABSTRACT

A pacemaker terminal for connecting an electrode lead having a proximal end includes a first section fixed to the pacemaker and a second section moveably engaged with the first section. A spring element is interposed between the first and second sections to exert a force to displace the moveable section from the fixed section. Both sections have transverse holes which, upon application of squeezing pressure to the terminal to overcome the spring action, become aligned so as to allow insertion of the proximal end of the electrode lead. Thereafter, upon release of the pressure, the spring element displaces the sections so as to capture the electrode lead securely in the holes. The holes may be provided with an internal thread, such as an asymmetrical sawtooth pattern, to aid in holding the lead in place and maintaining electrical contact with it.

18 Claims, 1 Drawing Sheet

PACEMAKER TERMINAL APPARATUS

BACKGROUND OF THE INVENTION

This invention relates to terminals for cardiac stimulators and, in particular, to implantable heart pacemaker devices.

In implantable heart pacemaker devices, pacemaker leads are connected to a patient's heart for acing or sensing cardiac electrical activity. The pacemaker lead is connected by its proximal end to a terminal on the pacemaker, and the distal end of the lead is disposed in suitable tissue. The precise location of the distal end may depend on factors, such as whether the lead is for sensing heart functions or for pacing such functions.

Existing pacemaker terminal devices, such as the device shown in U.S. Pat. No. 4,445,511 to Cowdery and Cooper, utilize connection of the pacemaker lead to the terminal by means of insertion of the proximal end of the lead into a lead hole in the terminal. The lead is then secured in this position in the terminal by means of screws commonly called "grub" screws.

One problem with pacemaker terminal devices which use grub screws is the inconvenience caused to a physician during implantation of the pacemaker device. It is during surgical implantation that the physician connects the pacemaker lead to the patient's heart and to the pacemaker terminal device. With terminal devices which use grub screws, the physician must first locate a slit at the top of the pacemaker terminal and then locate the screws, which are quite small, within the pacer header. Each grub screw is then screwed into the slit by means of a screwdriver. The screw connects with the pacemaker lead, which is inserted into the lead hole of the pacemaker. The force of the screw thus mechanically secures the pacemaker lead to the terminal.

As a part of this lengthy and tedious process, the screwdriver used to tighten the grub screws must, before insertion into the pacer header, be lubricated with a special lubricant which is supplied by the pacemaker manufacturer together with the lead and the screwdriver. Additionally, a problem sometimes occurs if the physician cannot readily find the exact location of the slit at the top of the pacemaker terminal. A further problem occurs when the grub screw head, which may be hexagon in shape, becomes distorted by excessive force, thereby making it difficult to perform the described procedure. Hence, there can be numerous inconveniences to physicians using the existing terminal devices.

A further problem with the use of grub screws for connecting leads in existing devices is the necessity for a slit for insertion of a screwdriver for screwing a grub screw. Such an opening represents a potential leakage path for the unwanted ingress of body fluids into the pacemaker terminal area. Such fluid leakage could impair proper operation of the pacemaker device.

SUMMARY OF THE INVENTION

It is an object of the invention to allow connection of electrode leads to a pacemaker while minimizing inconvenience to physicians at the time of both implantation and explantation of the pacemaker device.

It is a further object of the invention to eliminate the need for grub screws in pacemaker terminals and the need for an extra tool, such as a screwdriver, for connecting electrode leads to the pacemaker terminal.

It is a still further object of the invention to eliminate the need for screwdriver slits for terminals, thereby preventing the potentially problematic leakage of body fluids into pacemaker terminal areas.

It is a further object of the invention to provide a simple method permitting connecting and removing electrode leads in pacemaker devices.

According to the invention, there is provided a pacemaker terminal for connecting an electrode lead having a proximal end to a pacemaker. The terminal comprises: a first section having a first transverse hole, the first section adapted for being fixed to the pacemaker; a second section having a second transverse hole, the second section being moveably engageable with the first section for aligning the first transverse hole with the second transverse hole to receive the proximal end of the electrode lead; and means for springingly displacing the second section from the first section so as to move the first and the second transverse holes out of alignment and securely capture the proximal end of the electrode lead therein.

Further aspects of the present invention will become apparent from the following description and from the attached drawings, which are incorporated herein for purposes of describing the presently preferred embodiment of the invention.

DESCRIPTION OF THE PREFERRED EMBODIMENT

Figure 1:
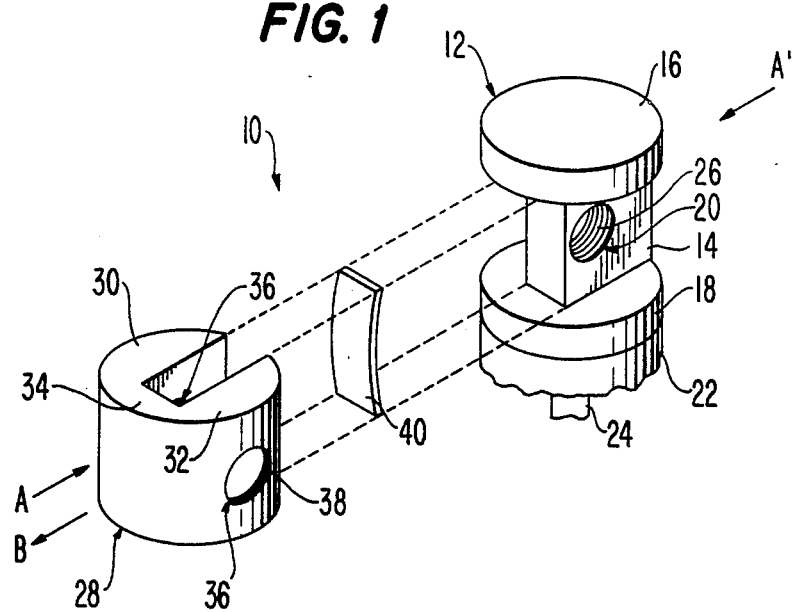
FIG. 1 is an exploded perspective view of a pacemaker terminal according to a preferred embodiment of the present invention.

The present invention will now oe explained with reference to the drawings, in which the same reference characters are used to designate like elements.

The present invention concerns a terminal, generally designated by reference character 10 in FIG. 1, for use with a pacemaker, such as of the implantable type. The terminal serves to connect the proximal end of an electrode lead (not shown in FIG. 1) to the pacemaker (not shown) in order to provide electrical interconnection between the pacemaker and tissue in which the distal end of the electrode lead is disposed.

According to the invention, the pacemaker terminal includes a first section having a first transverse hole, the first section being fixed to the pacemaker. As shown in FIG. 1, the first section is identified by reference character 12 and includes a neck portion 14 located between two abutting shoulder portions 16, 18. Neck portion 14 includes a hole 20 disposed transversely therethrough and having an inner diameter sufficient for accepting the proximal end of the electrode lead (not shown).

First section 12, comprising neck portion 14 and shoulders 16 and 18, may be integrally formed of a conductive material, such as tivanium or other suitable conductor. Tivanium is a somewhat harder material than titanium, which is commonly used for the proximal end of implantable electrode leads often employed with pacemakers. First section 12 is adapted to be fixedly mounted on the pacemaker (not shown) by a conventional arrangement, including a supporting insulating portion 22 and a feed through lead 24. Via lead 24, first section 12 can be electrically connected to circuitry (not shown) within the pacemaker which allows for electrical signals to be delivered to or from the electrode lead coupled to terminal 10. Structures suitable for mounting the first section on the pacemaker, including supporting insulating portion 22 (which may be a ceramic material) and lead 24, are known in the art and need not be described further for purposes of understanding the present invention.

Figure 2:
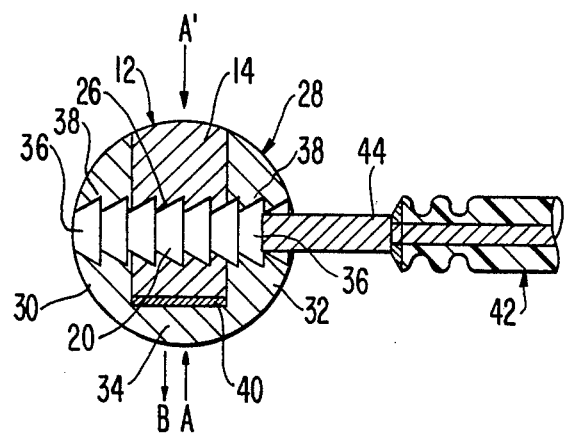
FIG. 2 shows a cross-section of a pacemaker terminal and a pacemaker lead according to the present invention.

According to a presently preferred embodiment, first hole 20 has an internal thread 26. Thread 26 may be a conventional thread, such as the type used for affixing screws, which is symmetrical in nature. Alternately, thread 26 may be asymmetrical; an example of an asymmetrical thread is shown in FIG. 2 in which a sawtooth configuration is employed. The purpose and function of this thread will be explained in detail hereinbelow.

Also according to the invention, a pacemaker terminal includes a second section having a second transverse hole, the second section being moveably engageable with the first section for aligning the first transverse hole with the second transverse hole to receive the proximal end of the electrode lead. A presently preferred embodiment of the second section is illustrated in FIG. 1 and is generally designated by reference character 28. Second section 28 may be formed of a conductive material, such as tivanium as described hereinabove.

In a preferred embodiment, second section 28 includes a pair of side portions 30 and 32, with an intermediate portion 34 joining the two side portions. A second hole 36 is provided transversely through each of side portions 30, 32. Hole 36 may be further provided with an internal thread 38 of the type described above with respect to first hole 20. That is, thread 38 may be either symmetrical or assymetrical, such as a sawtooth, in the same manner as previously described with respect to thread 26.

Second section 28 is configured to engage with first section 12, with side portions 30, 32 of second section 28 fitting on either side of the neck portion 14 of first section 12. When fully engaged in this fashion, second section 28 fits flush against shoulder portions 16 and 18 of first section 12 according to a preferred embodiment. Thus, shoulder sections 16 and 18 preferably each have a circumference or perimeter substantially equal to the circumference or perimeter of second portion 28 so that the overall terminal presents a relatively smooth, continuous cylindrical shape.

Furthermore, when fitted together in this fashion, second hole 36 in second section 28 is placed in total alignment with first hole 20 in the first section. Thus, the proximal end of the electrode lead (not shown in FIG. 1) can be disposed fully within both first and second transverse holes 20, 36 when aligned in this manner.

The present invention also includes means for springingly displacing the second section from the first section so as to move the first and the second transverse holes out of alignment and securely capture the proximal end of the electrode lead therein. As shown in FIG. 1 according to a preferred embodiment, the displacement means are generally designated by reference character 40 and comprise a spring formed of a canted piece of metal or other elastic material. Spring 40 is disposed between first and second sections 12, 28 proximate the neck portion 14 and the intermediate portion 34. Spring 40 is further maintained in place by the presence of abutting shoulder portions 16 and 18, which have respective flanges that extend beyond the width of neck portion 14 of the first section 12.

Operation of the terminal apparatus according to the present invention will now be explained with reference to FIGS. 1 and 2. When moveable section 28 is normally engaged with fixed section 12, lead holes 20 and 36 are not in direct alignment due to the action of spring 40 interposed between the two sections. In order to insert a pacemaker lead into the terminal holes, it is first necessary to achieve alignment between holes 20 and 36. Such alignment of the terminal holes is achieved by pressing or squeezing moving section 28 of terminal 10 towards fixed section 12 in opposition to the force exerted by spring 40.

The pressing or squeezing pressure is applied in the direction of the arrows A and A' as shown in FIGS. 1 and 2. The pressure can be provided by the physician squeezing terminal apparatus 10 with his or her fingers, or by other suitable mechanical arrangements. This action overcomes the displacement of section 34 from section 12 and permits holes 20, 36 to be aligned. Proximal end 44 of an electrode lead 42 FIG. 2) can then be easily inserted into the terminal holes once aligned in this manner.

After insertion of the pacemaker lead, the external pressure is released, thus allowing spring 40 to exert force in an effort to resume its normal canted shape. The force exerted by spring 40 in this fashion causes second section 28 to move away from fixed first section 12 in the direction indicated by arrow B in FIGS. 1 and 2. With such movement, holes 20 and 36 are forced slightly out of alignment, thereby causing the proximal end 44 of the lead 42 to be securely fixed into the terminal. As a result, there is a very effective electrical contact in addition to a very secure mechanical fixation between the pacemaker lead and the terminal.

Lead 42 is released by again pressing or squeezing the terminal 10 in the direction of the arrows A and A'. As previously explained with respect to the step of insertion, this pressure flattens canted spring 44 and causes alignment of holes 20 and 36. The pacemaker lead is then easily removed from the terminal 10.

Although it is not essential that the internal surfaces of holes 20 and 36 be threaded, it is preferable that such surfaces be threaded in order to achieve a more efficient electrical contact as well as secure mechanical fixation. According to a presently preferred embodiment of the invention, the threads are asymmetrical in nature, namely, the sawtooth configuration illustrated in FIG. 2. Other arrangement of threads or other internal protrusions within either or both of lead holes 20, 36 may be used without departing from the spirit or scope of the invention.

One particular advantage of the configuration as shown in FIGS. 1 and 2 is its capability of directly replacing existing terminals having grub screws and providing an easy assembly procedure when the flexible pacemaker header portion is added to the terminal assembly.

The invention is particularly advantageous for certain pacer top configurations, such as quadripolar tops for thin pacemakers. Grub screws may not be used with these pacemakers, since their thin configuration prevents side entry.

The spring in the existing embodiment is not limited to the one as shown in the drawings. Other elements capable of providing spring action can be used, such :s coiled or leaf springs, or metallic elements bent into other than a canted shape. It is also recognized that compressible non-metallic materials can be used to provide the necessary spring action, such as a thin piece of rubber interposed between neck portion 14 of fixed section 12 and intermediate portion 34 of moveable section 28. Accordingly, various changes can be made with regard to the displacing means without departing from the spirit or scope of the invention.

Although the invention has been described with reference to a particular embodiment, it is to be understood that this embodiment is merely illustrative of the application of the principles of the invention. Numerous modifications may therefor be devised without departing from the spirit and scope of the invention.

What is claimed is:

1. A pacemaker terminal for connecting an electrode lead having a proximal end to a pacemaker, comprising:
   a first section having a first transverse hole;
   a second section having a second transverse hole, said second section being moveably engageable with said first section for aligning said first transverse hole with said second transverse hole to receive the proximal end of the electrode lead; and
   means for springingly displacing said second section from said first section so as to move said first and said second transverse holes out of alignment and securely capture the proximal end of the electrode lead therein, said displacing means comprising a canted metallic spring interposed between said first and second sections.

2. A pacemaker terminal as recited in claim 1, wherein said first transverse hole includes an internal thread.

3. A pacemaker terminal as recited in claim 2, wherein said internal thread is symmetrical.

4. A pacemaker terminal as recited in claim 2, wherein said internal thread is asymmetrical.

5. A pacemaker terminal as recited in claim 1, wherein said second transverse hole includes an internal thread.

6. A pacemaker terminal as recited in claim 5, wherein said internal thread is symmetrical.

7. A pacemaker terminal as recited in claim 6, wherein said internal thread is asymmetrical.

8. A pacemaker terminal for connecting an electrode lead having a proximal end to a pacemaker, comprising:
   a first section having a neck portion with a first hole transversely therethrough;
   a second section having a pair of side portions with a second hole transversely therethrough and an intermediate portion joining said side portions, said second section being moveably disposed on said first section with said side portions engaging said neck portion for aligning said first hole with said second hole to receive the proximal end of the electrode lead therein; and
   means for sparingly displacing said second section from said first section so as to move said first and second holes out of alignment and securely capture the proximal end of the electrode lead therein, said displacing means comprising a canted metallic spring interposed between said intermediate portion of said second section and said neck portion of said first section.

9. A pacemaker terminal as recited in claim 8, wherein said first section includes a pair of shoulder portions abutting said neck portion.

10. A pacemaker terminal as recited in claim 9, wherein said second section is dimensioned so as to fit flushly about said neck portion of said first section between said pair of shoulder portions when said first and second holes are aligned.

11. A pacemaker terminal as recited in claim 9, wherein said second section and said pair of shoulder portions have substantially equal outer perimeter dimensions.

12. A pacemaker terminal as recited in claim 8, wherein said first hole includes an internal thread.

13. A pacemaker terminal as recited in claim 12, wherein said internal thread is symmetrical.

14. A pacemaker terminal as recited in claim 12, wherein said internal thread is asymmetrical.

15. A pacemaker terminal as recited in claim 8, wherein said second hole includes an internal thread.

16. A pacemaker terminal as recited in claim 15, wherein said internal thread is symmetrical.

17. A pacemaker terminal as recited in claim 15, wherein said internal thread is asymmetrical.

18. A pacemaker terminal as recited in claim 8 wherein said first and second holes each includes an internal thread.

* * * * *